(12) United States Patent
Yamaji et al.

(10) Patent No.: US 8,741,334 B2
(45) Date of Patent: Jun. 3, 2014

(54) EXTERNAL PLASTER CONTAINING FLURBIPROFEN

(75) Inventors: Masahiro Yamaji, Kagawa (JP); Takaya Sugawara, Kagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 1089 days.

(21) Appl. No.: 11/817,210

(22) PCT Filed: Feb. 28, 2005

(86) PCT No.: PCT/JP2005/003280
§ 371 (c)(1),
(2), (4) Date: Nov. 19, 2007

(87) PCT Pub. No.: WO2006/092829
PCT Pub. Date: Sep. 8, 2006

(65) Prior Publication Data
US 2009/0022778 A1   Jan. 22, 2009

(51) Int. Cl.
*A61K 9/70* (2006.01)
*A61K 31/34* (2006.01)
*A61F 13/00* (2006.01)
*A01N 43/08* (2006.01)

(52) U.S. Cl.
USPC .......................................... 424/443; 514/470

(58) Field of Classification Search
CPC ............................. A61K 9/7076; A61K 31/00
USPC .......................................... 424/443; 514/470
See application file for complete search history.

(56) References Cited

U.S. PATENT DOCUMENTS

| 5,478,567 | A | 12/1995 | Nakagawa et al. |
| 5,776,484 | A | 7/1998 | Sasaki et al. |
| 5,869,087 | A | 2/1999 | Hirano et al. |
| 7,094,421 | B2 | 8/2006 | Akazawa et al. |

FOREIGN PATENT DOCUMENTS

| EP | 1623711 | A1 | 2/2006 |
| JP | 56-154413 | A | 11/1981 |
| JP | 07-144017 | A | 6/1995 |
| JP | 07-309749 | A | 11/1995 |
| JP | 08-165251 | A | 6/1996 |
| JP | 08-295624 | A | 11/1996 |
| JP | 08-319234 | A | 12/1996 |
| JP | 11-199515 | A | 7/1999 |
| JP | 2002-226336 | A | 8/2002 |
| JP | 2003-183156 | A | 7/2003 |
| JP | 2004-043512 | A | 2/2004 |
| JP | 2004-083462 | A | 3/2004 |
| JP | 2004-315542 | A | 11/2004 |

OTHER PUBLICATIONS

English Translation of JP 08-319234; published: Dec. 3, 1996; Tables 1 and 2 on p. 4.*
English Translation of the International Preliminary Report on Patentability, filing: Feb. 28, 2005.
International Search Report for PCT/JP2005/003280, Apr. 6, 2005.

* cited by examiner

*Primary Examiner* — Johann R Richter
*Assistant Examiner* — Genevieve S Alley
(74) *Attorney, Agent, or Firm* — Ostrager Chong Flaherty & Broitman PC

(57) ABSTRACT

In a plaster for external use for transdermal absorption in which an adhesive layer is laminated on a plastic backing, the adhesive layer contains a styrene-isoprene-styrene block copolymer (SIS), a tackifying resin and a softener which are essential ingredients, and further contains flurbiprofen blended as an active ingredient. The present plaster for external use is a flurbiprofen containing plaster for external use enabling long-term stable release of contained flurbiprofen, and having excellent stability and very high drug releasing property.

4 Claims, 3 Drawing Sheets

EXTERNAL PLASTER CONTAINING FLURBIPROFEN

The present application is the U.S. national phase application corresponding to and claiming the priority of International Application PCT No. PCT/JP2005/003280, filed Feb. 28, 2005, which is incorporated by reference.

TECHNICAL FIELD

The present invention relates to a plaster for external use which comprises an adhesive containing a styrene-isoprene-styrene block copolymer (SIS), a tackifying resin and a softener, which are all essential ingredients, and flurbiprofen blended therein as an active ingredient.

BACKGROUND ART

Flurbiprofen which is one kind of nonsteroidal anti-inflammatory drugs (NSAIDs) is a drug having wide applicability to chronic rheumatism, osteoarthritis deformans, omarthritis, lumbago, tendovaginitis, muscle pain and the like, and is administered orally in the dosage forms of tablet, granules and the like, or transdermally in the dosage forms of ointment, plasters and the like.

Preparations for oral administration disadvantageously cause appearance of side effect such as gastrointestinal damage specifically observed in NSAIDs, and decrease in drug efficacy because the drug having absorbed in the body is metabolized and decomposed in early stage by liver.

Contrarily, preparations for transdermal administration do not cause side effect and drug metabolism in liver as is the case of oral preparations, and enable constant supply of drug into a body in continuous manner for a long term.

In view of the above, with regard to flurbiprofen, transdermally absorbable preparations that will not pass along a gastrointestinal tract, liver and the like attract the attention, and among such preparations, plasteres for external use attract attentions for their excellent continuity of drug release, and easiness of handling, and several attempts have been made heretofore.

For example, Patent Document 1 (Japanese Patent Laid-Open Publication No. Sho 56-154413) and Patent document 2 (Japanese Patent Laid-Open Publication No. Hei 11-199515) disclose cataplasm using a water-soluble polymer containing flurbiprofen as an active ingredient. However, since such cataplasm contains a large amount of water, flurbiprofen, which is an active ingredient, is difficult to be blended in a high concentration, and transdermal absorption of drug is poor, and it cannot be mentioned that sufficient drug efficacy is obtained.

For compensating such drawbacks of cataplasm, several reports of plasteres using rubber-based adhesives have been made. For example, Patent Document 3 (Japanese Patent Laid-Open Publication No. Hei 8-319234) reports a plaster, which contains an adhesive, made up of a rubber component, a tackifying resin and a softener, and flurbiprofen blended therein. However, the adhesive constituting the plaster of Patent Document 3 little contains a component that dissolves flurbiprofen, so that flurbiprofen is dispersed in crystal forms in the preparation. Therefore, it is conceivable that drug releasability would be very poor.

Patent Document 4 (WO 93/04677), which uses other rubber-based adhesive, discloses a tape-type preparation containing 1-menthol as a resolvent for flurbiprofen. However, volatile 1-menthol vaporizes during storage, and crystals of flurbiprofen, which is a principal agent, may be generated.

Furthermore, Patent Document 5 (Japanese Patent Laid-Open Publication No. Hei 7-309749) reports a rubber-based adhesive using lactic acid ester as a resolvent for flurbiprofen, however, such resolvent may leave residual adhesive on skin due to destruction of cohesive power of adhesive when the preparation is detached, and may give skin irritation.

Patent Document 1: Japanese Patent Laid-Open Publication No. Sho 56-154413

Patent Document 2: Japanese Patent Laid-Open Publication No. Hei 11-199515

Patent Document 3: Japanese Patent Laid-Open Publication No. Hei 8-319234

Patent Document 4: WO 93/04677

Patent document 5: Japanese Patent Laid-Open Publication No. Hei 7-309749

DISCLOSURE OF THE INVENTION

Problems to be Solved by the Invention

In light of the current state of art as described above, it is an object of the present invention to provide a flurbiprofen-containing plaster for external use having excellent transdermal absorptivity of flurbiprofen, excellent stability as a preparation, and giving extremely little skin irritation.

Means for Solving the Problem

In order to solve such problems, the present inventors made diligent effort to find that by blending flurbiprofen, which is an active ingredient, into a base (adhesive layer) containing a styrene-isoprene-styrene block copolymer (hereinafter, also referred to as "SIS"), a tackifying resin and a softener which are essential ingredients, the problems as described above can be solved at a blow, and finally accomplished the present invention.

Specifically, a basic aspect of the present invention is a plaster for external use in which an adhesive layer is laminated on a backing, wherein the adhesive layer contains 5 to 50% by weight of a styrene-isoprene-styrene block copolymer (SIS), 20 to 70% by weight of a tackifying resin, and 5 to 60% by weight of a softener which are essential ingredients, and further contains flurbiprofen blended as an active ingredient.

More specifically, the present invention provides a plaster for external use, wherein the tackifying resin is a rosin-based resin, and a blending amount of the rosin-based resin with respect to flurbiprofen is 10 times or more by weight ratio.

Also, the present invention provides a plaster for external use, wherein the softener is liquid paraffin.

Therefore, the most preferred aspect of the present invention is a plaster for external use in which an adhesive layer is laminated on a backing, wherein the adhesive layer contains 10 to 30% by weight of a styrene-isoprene-styrene block copolymer (SIS), 20 to 70% by weight of a rosin resin, and 10 to 50% by weight of a liquid paraffin which are essential ingredients, and further contains flurbiprofen blended as an active ingredient, and a blending amount of the rosin resin with respect to flurbiprofen is 10 times or more by weight ratio.

In other words, one feature of the present invention is to use a styrene-isoprene-styrene block copolymer, a tackifying resin and a softener as essential ingredients of the adhesive layer of the plaster containing flurbiprofen.

Other feature lies in blending such components in combination of respective certain specified amounts, and in particular, in blending a tackifying resin for flurbiprofen in a specific weight ratio or more.

Effect of the Invention

In the flurbiprofen-containing plaster for external use provided by the present invention, the adhesive layer contains a styrene-isoprene-styrene block copolymer, a tackifying resin and a softener which are essential ingredients and blended in respective specified proportions, so that crystal deposition of flurbiprofen into the adhesive layer is prevented. As a result, it becomes possible to transdermally administer flurbiprofen, which is an active ingredient, stably for a long time with high releasability.

Furthermore, by blending a specific weight ratio or more of a tackifying resin, especially rosin rein with respect to flurbiprofen, preparation can be stabilized, and crystal deposition of flurbiprofen, which is an active ingredient into an adhesive layer, is prevented, and stable transdermal absorption is realized.

BEST MODE FOR CARRYING OUT THE INVENTION

Figure 1:
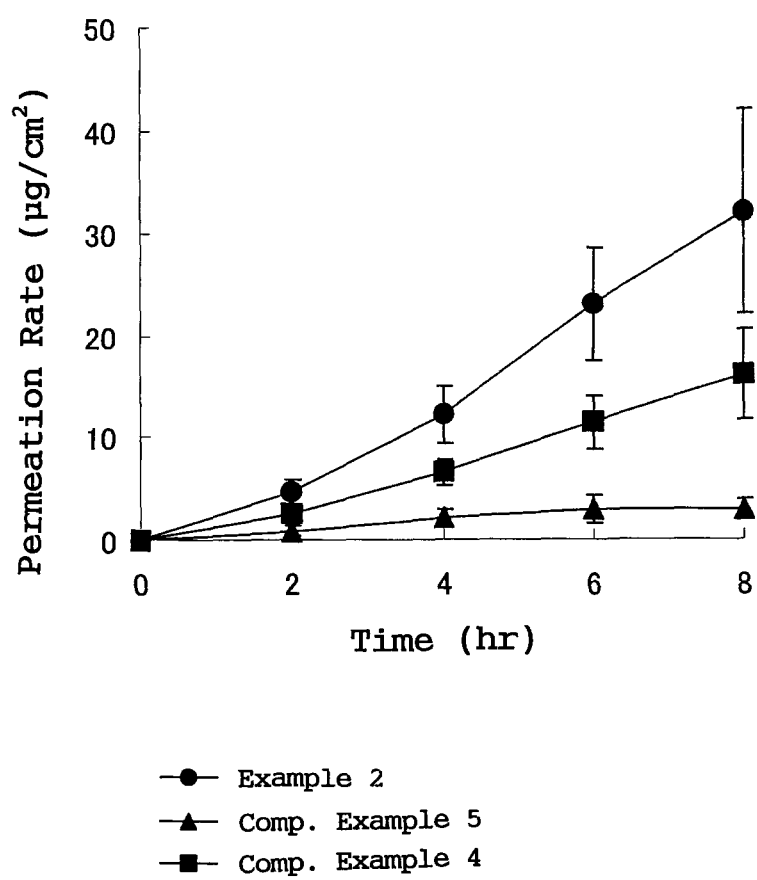
FIG. 1 is a chart showing results of drug release test (rat in-vitro permeation test) of Test example 2, and results about plasters of Example 2 of the present invention, and Comparative examples 4 and 5.

In the plaster for external use provided by the present invention, blending amount of SIS, which is used as an adhesive layer (base) component, is 5 to 50% by weight, preferably 10 to 30% by weight, and more preferably 15 to 20% by weight. Blending amount of less than 5% by weight is not preferred because cohesive power of base is insufficient so that a problem arises that the base remains on skin after removing the plaster. Conversely, blending amount of more than 50% by weight is not preferable because cohesion power of base is so high that decrease in adhesion power or difficulty of kneading operation is caused.

Usually, the a tackifying resin imparts skin adhesivity to the base when mixed with SIS, and as such, rosin-based resin, petroleum-based resin, terpene resin or the like is used. In the present invention, it is essential to use a rosin-based resin as a tackfier resin for dissolving flurbiprofen and preventing crystallization of drug in the preparation. As such a rosin-based resin, rosin ester, hydrogenated rosin, glycerin rosin ester, hydrogenated rosin glycerin ester, rosinic acid, polymerized rosin and the like can be exemplified.

Among these, hydrogenated rosin glycerin ester is particularly preferred. Desirable blending amount is 10 times or more, and more preferably 15 times or more of blending amount of flurbiprofen.

In order to improve the adhesive property of the plaster, desired blending amount into the adhesive layer is 20 to 70% by weight, preferably 30 to 60% by weight, and more preferably 40 to 50% by weight. Blending amount of less than 20% by weight is not preferable because adhesive property of the plaster is poor, and blending amount of more than 70% by weight is not preferable because adhesive tack is so strong that physical skin irritation is caused when the plaster is removed from the skin.

The softener blended into the adhesive layer softens the adhesive, thereby improving the own skin followability of the plaster, adjusting the adhesive power and reducing physical skin irritation.

As the softener for use in the present invention, paraffin-based oil, silicone oil, higher fatty acid, vegetable oil, polybutene and the like are exemplified, and liquid paraffin is particularly preferred. Its blending amount is 5 to 60% by weight, preferably 10 to 50% by weight, and more preferably 20 to 40% by weight. When the blending amount is less than 5% by weight, its skin followability is poor and the plaster is easy to be released, and when the blending amount is more than 60% by weight, the cohesive power of adhesive is impaired and the adhesive remains in the adhered site.

In the plaster for external use provided by the present invention, blending amount of flurbiprofen, which is contained as an active ingredient, is 0.5 to 5% by weight, and preferably 1 to 3% by weight.

When the blending amount is less than 0.5% by weight, the expected drug efficacy is difficult to be obtained because the absolute release amount of drug is small. Blending amount of more than 5% by weight is not preferable, because it is necessary to greatly increase the blending amount of the tackifying resin for preventing crystallization of flurbiprofen, and therefore, skin irritation due to increase in adhesive power of the plaster for external use is enhanced.

In the plaster for external use of the present invention, conventionally used components that are usually used in preparing a plaster may be appropriately added besides the above components. For example, antioxidants such as dibutylhydroxytoluene (BHT), titanium oxide, silicon dioxide and the like fillers may be used.

The adhesive layer in the plaster for external use of the present invention has a thickness of, but not particularly limited to, about 50 μm to 300 μm. More preferably, it is about 100 μm to 200 μm. Too small thickness of adhesive layer will decrease the adhesive power, and too large thickness is not preferred because the drug that is not used in the adhesive mass increases, and thus the cost rises, and becomes easy to peel of due to friction with cloths.

It is generally proved that in a plaster for external use, the flexibility and stretchability of backing influence on the skin followability, and greatly participate in improvement of transdermal absorption of drug. Therefore, in the plaster for external use of the present invention, it is preferred to use a backing having high flexibility and stretchability, and as such a backing, nonwoven fabric, or woven fabric is exemplified, and polyester nonwoven fabric or woven fabric, in which the absorptivity of drug itself is small, is preferably used.

As the release liner used in the plaster for external use of the present invention, polyethylene terephthalate, polypropylene, paper or the like is exemplified, with polyethylene terephthalate being particularly preferred. The release liner may be subjected to silicone treatment as is necessary for optimizing the release strength.

The plaster for external use provided by the present invention may be produced, for example, in a manner as described below.

Concretely, SIS, a softener and a tackfier agent constituting an adhesive layer, and additionally an antioxidant, a filler and the like as appropriate are melted under heating. Then flurbiprofen, which is a principal agent, is added to the above adhesive, and mixed under stirring, to prepare an adhesive mass for the plaster.

The adhesive mass thus prepared is spreaded on silicone-processed polyethylene terephthalate film, to form an adhesive layer having a thickness of 50 to 300 μm. The obtained adhesive layer is laminated with a polyester woven fabric or nonwoven fabric which is a backing, and then the resultant article is cut into a desired size and shape, and thus a transdermal adsorptive preparation of the present invention is obtained.

EXAMPLES

Next, the present invention will be explained more specifically by way of concrete examples, however, the present invention is not limited to the following examples.

In the following examples, blending amount is indicated by "part(s) by weight" unless otherwise specified.

Examples 1 to 4/Comparative Examples 1 to 3

According to the production method as described above, plasteres based on formulations shown in Table 1 (Examples 1 to 4) and Table 2 (Comparative Examples 1 to 3) were obtained.

TABLE 1

| Composition | Example | | | |
|---|---|---|---|---|
| | 1 | 2 | 3 | 4 |
| SIS | 25 | 15 | 12 | 10 |
| Rosin resin | 30 | 40 | 50 | 60 |
| Liquid paraffin | 41 | 40 | 32 | 23 |
| BHT | 2 | 2 | 2 | 2 |
| Flurbiprofen | 2 | 3 | 4 | 5 |

TABLE 2

| Composition | Comparative Example | | |
|---|---|---|---|
| | 1 | 2 | 3 |
| SIS | 15 | 15 | 15 |
| Rosin resin | 30 | — | — |
| Alicyclic saturated hydrocarbon resin | — | 40 | — |
| Terpene resin | — | — | 40 |
| Liquid paraffin | 46 | 40 | 40 |
| BHT | 2 | 2 | 2 |
| Flurbiprofen | 7 | 3 | 3 |

Comparative Example 4

Cataplasm Using Water-Soluble Base Such as Polyacrylic Acid

As a plaster of Comparative Example 4, commercially available Adfeed (registered trademark) which is cataplasm using a water-soluble base such as polyacrylic acid, and containing 0.33% of flurbiprofen was used.

Comparative Example 5

Tape Using Natural Rubber Latex

As a plaster of Comparative Example 5, commercially available FLUPE TAPE (registered trademark), which is a tape using natural rubber latex containing 2.86% of flurbiprofen, was used.

Test Example 1

Crystal Deposition Test

Plasteres obtained in Examples 1 to 4, and in Comparative Examples 1 to 3 were cut into an appropriate size of square pieces, and each piece was packed in a bag of aluminum laminate. In such a state, the piece was stored in various temperature conditions, and an adhesive layer was observed visually or under microscope with time, and deposition state of crystals of flurbiprofen which is an active ingredient into the adhesive layer was observed.

The results are shown in Table 3.

TABLE 3

| Stored sample (Stored plaster) | Storage period | | |
|---|---|---|---|
| | 1 week | 1 month | 3 months |
| Example 1 | — | — | — |
| Example 2 | — | — | — |
| Example 3 | — | — | — |
| Example 4 | — | — | — |
| Comparative Example 1 | — | ○ | ○ |
| Comparative Example 2 | ○ | ○ | ○ |
| Comparative Example 3 | ○ | ○ | ○ |

—: Deposition of crystals not observed
○: Deposition of crystals observed

As is apparent from the results shown in Table, in the plasteres of Examples 1 to 4 of the present invention, deposition of crystals of flurbiprofen which is an active ingredient was not observed in the adhesive layer during storage of three months.

Contrary to the above results, in the plasteres of Comparative Example 2 and Comparative Example 3, deposition of crystals of flurbiprofen was observed after one week in room temperature storage condition, and in the plaster of Comparative Example 1 deposition of crystals of flurbiprofen was observed after one month.

These results demonstrate that the plaster for external use of the present invention is a very stable preparation in which deposition of crystals of flurbiprofen which is an active ingredient is not observed in an adhesive layer.

Test Example 2

Drug Release Test (Rat In-Vitro Permeation Test)

In order to examine the drug releasability of flurbiprofen depending on the particular bases (adhesive layer), rat in-vitro permeability test was conducted using plasteres of Example 2 of the present invention, and commercially available plasteres of Comparative Example 4 and Comparative Example 5.

Similar rat in-vitro permeability test was conducted for plasteres of Example 2, Comparative Examples 1, 2 and 3 after storage of one month.

(Method)

Abdomen excised skin of depilated rat was set in a Franz cell, and the interior was charged with phosphate-buffered saline, and the water jacket was refluxed with warm water of 37° C. Each plaster was punched into a circular shape (1.77 cm$^2$), and was adhered to rat excised skin. Receptor liquid was sampled with time, and a permeation amount of flurbiprofen which is an active ingredient was measured by liquid chromatography.

(Results)

Figure 2:
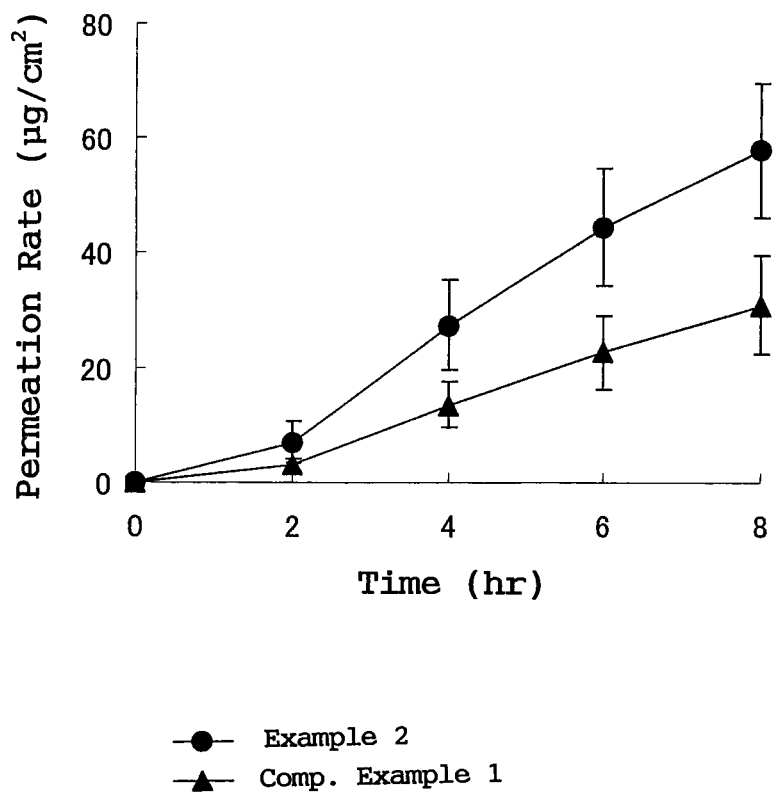
FIG. 2 is a chart showing results of drug release test (rat in-vitro permeation test) of Test example 2, and results about plasters of Example 2 and Comparative example 1 after storage of one month.
Figure 3:
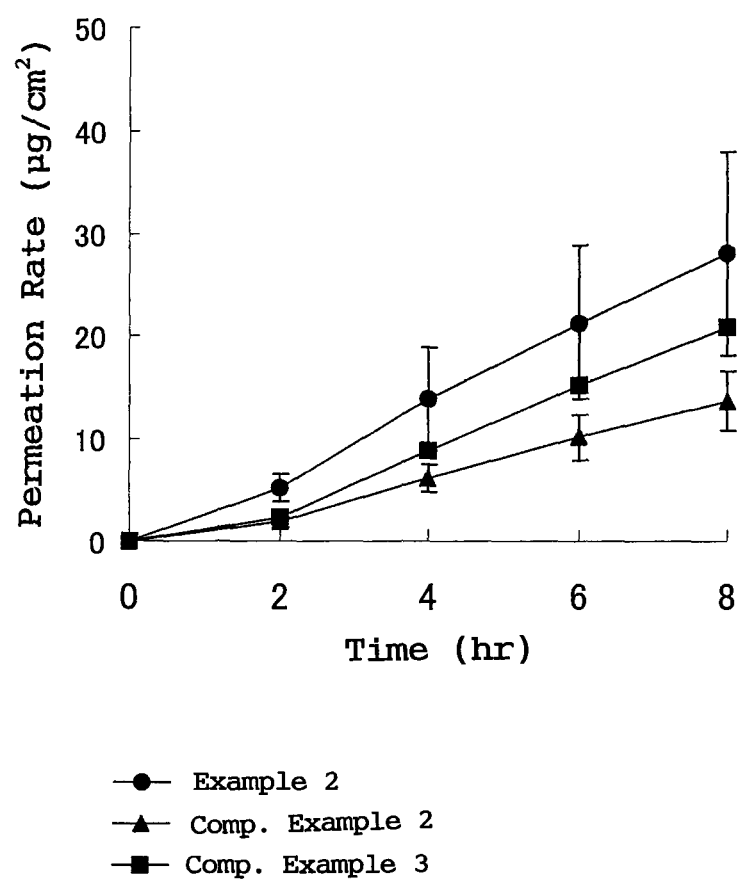
FIG. 3 is a chart showing results of drug release test (rat in-vitro permeation test) of Test example 2, and results about plasters of Example 2 and Comparative examples 2 and 3 after storage of one month.

Results are shown in FIG. 1 to FIG. 3. FIG. 1 is a view showing results of plasters in Example 2 of the present invention, and in Comparative Examples 4 and 5 which are commercially available products. The plaster of Example 2 showed much higher drug permeation amount than the plasteres of Comparative Example 4 and Comparative Example 5 (commercially available products) using other bases.

FIG. 2 and FIG. 3 show results of the plaster of Example 2, the plaster of Comparative Example 1 (FIG. 2), and the plasteres of Comparative Example 2 and Comparative Example 3 (FIG. 3) after storage of one month. In the plasteres of Comparative Examples 1, 2 and 3, drug permeation amounts are much lower than that of Example 2 because crystals of flurbiprofen deposit in the adhesive layer occurred during storage.

These results demonstrate that the present invention provides a stable plaster having high drug releasability by inhibiting crystallization of flurbiprofen which is an active ingredient of the plaster in an adhesive layer.

Industrial Applicability

As described above, the plaster provided by the present invention is a plaster for external use which includes an adhesive layer containing a styrene-isoprene-styrene block copolymer (SIS), a tackifying resin and a softener which are essential ingredients, and further contains flurbiprofen blended as an active ingredient, and the plaster enables long-term stable releasability of flurbiprofen and has very high drug releasability, so that it is very useful in the medical field.

The invention claimed is:

1. A plaster for external use in which an adhesive layer is laminated on a backing, wherein the adhesive layer consists of 5 to 50% by weight of a styrene-isoprene-styrene block copolymer (SIS), 20 to 70% by weight of a tackifying resin, and 5 to 60% by weight of a softener, and wherein flurbiprofen as an active ingredient is blended in said adhesive layer, and further wherein a blending amount of the rosin-based resin with respect to flurbiprofen is 10 times or more by weight ratio.

2. The plaster for external use according to claim 1, wherein the softener is a liquid paraffin.

3. A plaster for external use in which an adhesive layer is laminated on a backing, wherein the adhesive layer consists of 10 to 30% by weight of a styrene-isoprene-styrene block copolymer (SIS), 20 to 70% by weight of a rosin resin, and 10 to 50% by weight of a liquid paraffin, and wherein flurbiprofen as an active ingredient is blended in said adhesive layer, and further wherein a blending amount of the rosin resin with respect to flurbiprofen is 10 times or more by weight ratio.

4. A plaster for external use in which an adhesive layer is laminated on a backing, wherein the adhesive layer consists of 5 to 50% by weight of a styrene-isoprene-styrene block copolymer (SIS), 30 to 60% by weight of a rosin resin, 5 to 60% by weight of a softener, and BHT, and wherein flubiprofen as an active ingredient is blended in said adhesive layer, and further wherein a blending amount of the rosin-based resin with respect to flubiprofen is 10 times or more by weight ratio and wherein the plaster is substantially free of flurbiprofen crystals.

* * * * *

UNITED STATES PATENT AND TRADEMARK OFFICE
CERTIFICATE OF CORRECTION

| | |
|---|---|
| PATENT NO. | : 8,741,334 B2 |
| APPLICATION NO. | : 11/817210 |
| DATED | : June 3, 2014 |
| INVENTOR(S) | : Yamaji et al. |

Page 1 of 1

It is certified that error appears in the above-identified patent and that said Letters Patent is hereby corrected as shown below:

In the Claims

Claim 1, Column 8, line 9;

delete "tackifying" and insert --rosin-based--, therefor

Claim 4, Column 8, line 28;

delete "rosin" and insert --rosin-based--, therefor

Claim 4, Column 8, line 29-30;

delete "flubiprofen" and insert --flurbiprofen--, therefor

Claim 4, Column 8, line 32;

delete "flubiprofen" and insert --flurbiprofen--, therefor

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,741,334 B2 | Page 1 of 1 |
| APPLICATION NO. | : 11/817210 | |
| DATED | : June 3, 2014 | |
| INVENTOR(S) | : Yamaji et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1191 days.

Signed and Sealed this
Twenty-eighth Day of July, 2015

Michelle K. Lee
*Director of the United States Patent and Trademark Office*